(12) United States Patent
Gambari et al.

(10) Patent No.: US 7,659,258 B2
(45) Date of Patent: Feb. 9, 2010

(54) DOUBLE-STRANDED SYNTHETIC OLIGONUCLEOTIDES USEFUL FOR INDUCING APOPTOSIS OF OSTEOCLASTS FOR THE TREATMENT OF OSTEOPENIC PATHOLOGIES

(75) Inventors: Roberto Gambari, Bologna (IT); Letizia Penolazzi, Ferrara (IT); Roberta Piva, Ferrara (IT)

(73) Assignees: Universita' Degli Studi di Ferrara, Ferrara (IT); Associazione Veneta per la Lotta Alla Talassemia, Rovigo (IT)

( * ) Notice: Subject to any disclaimer, the term of this patent is extended or adjusted under 35 U.S.C. 154(b) by 130 days.

(21) Appl. No.: 11/910,086

(22) PCT Filed: Mar. 30, 2006

(86) PCT No.: PCT/IB2006/000741

§ 371 (c)(1),
(2), (4) Date: Sep. 28, 2007

(87) PCT Pub. No.: WO2006/117600

PCT Pub. Date: Nov. 9, 2006

(65) Prior Publication Data

US 2008/0171717 A1    Jul. 17, 2008

(30) Foreign Application Priority Data

Mar. 31, 2005 (IT) ............ TO2005A0212

(51) Int. Cl.
C07H 21/04 (2006.01)
C07H 21/02 (2006.01)
A61K 31/70 (2006.01)
C12Q 1/68 (2006.01)
C12N 5/00 (2006.01)

(52) U.S. Cl. ............ 514/44; 536/23.1; 536/24.1; 536/24.5

(58) Field of Classification Search ............ None
See application file for complete search history.

(56) References Cited

OTHER PUBLICATIONS

Lambertini, et al., "Osteoblastic Differentiation Induced by Transcription Factor Decoy against Estrogen Receptor α Gene," Biochemical and Biophysical Research Communications 292, pp. 761-770 (2002).

Matsuzaki, et al., "Human Osteoclast-Like Cells Are Formed from Peripheral Blood Mononuclear Cells in a Coculture with SaOS-2 Cells Transfected with the Parathyroid Hormone (PTH)/PTH-Related Protein Receptor Gene," Endocrinology vol. 140, No. 2, pp. 925-932, copyright 1999 by The Endocrine Society.

Piva, et al., "Modulation of Estrogen Receptor Gene Transcription in Breast Cancer Cells by Liposome Delivered Decoy Molecules," Journal of Steroid Biochemistry & Molecular Biology 75 (2000) pp. 121-128.

Boatright, et al., "Mechanisms of Caspase Activation," Current Opinion in Cell Biology, 2003, pp. 725-731.

Lambertini E et al., "Modulation of gene expression in human osteoblasts by targeting a distal promoter region of human estrogen receptor-alpha gene", Journal of Endocrinology, Mar. 2002, pp. 683-693, vol. 172, No. 3, XP002413954, ISSN: 0022-0795.

Penolaiii Letizia, et al., "Peptide nucleic acid-DNA decoy chimeras targeting NF-kappaB transcription factors: Induction of apoptosis in human primary osteoclasts", International Journal of Molecular Medicine, Aug. 2004, pp. 145-152, vol. 14, No. 2, XP008073371, ISSN: 1107-3756.

Penolaiii Letizia, et al., "Cis element 'decoy' against the upstream promoter of human estrogen receptor gene", Biochimica et Biophysica Acta. Gene Structure and Expression, Jul. 2000, pp. 560-567, vol. 1492, No. 2-3, XP004275731, ISSN: 0167-4781.

Penolaiii Letizia, et al., "Decoy oligodeoxynucleotides targeting NF-kappaB transcription factors: Induction of apoptosis in human primary osteoclasts.", Biochemical Pharmacology, Oct. 2003, pp. 1189-1198, vol. 66, No. 7, XP002413955, ISSN: 0006-2952.

Piva R et al., "Induction of apoptosis of human primary osteoclasts treated with a transcription factor decoy mimicking a promoter region of estrogen receptor [alpha]", Apoptosis, An International Journal on Programmed Cell Death, Oct. 2005, pp. 1079-1094, vol. 10, No. 5, XP019204744, ISSN: 1573-675X.

*Primary Examiner*—Sean R McGarry
(74) *Attorney, Agent, or Firm*—Sughrue Mion, PLLC

(57) ABSTRACT

The invention relates to a synthetic double-stranded oligonucleotide capable of modifying the molecular phenotype of osteoclasts and increasing the expression of the oestrogen alpha receptor gene. Pharmaceutical compositions comprising the oligonucleotide according to the invention are also described, as well as therapeutic applications of that oligonucleotide, in particular for the treatment of osteopenic diseases such as for example osteoporosis. The oligonucleotide according to the invention is characterized in that it comprises the sequence 5'-ATTTATTTTCAATACTGACT-3' (SEQ ID NO: 1) or a fragment or a mutant thereof.

7 Claims, No Drawings

SEQUENCE LISTING

<160> NUMBER OF SEQ ID NOS: 5

<210> SEQ ID NO 1
<211> LENGTH: 20
<212> TYPE: DNA
<213> ORGANISM: Homo sapiens

<400> SEQUENCE: 1
atttattttc aatactgact                                             20

<210> SEQ ID NO 2
<211> LENGTH: 20
<212> TYPE: DNA
<213> ORGANISM: Homo sapiens

<400> SEQUENCE: 2
taaataaaag ttatgactga                                             20

<210> SEQ ID NO 3
<211> LENGTH: 20
<212> TYPE: DNA
<213> ORGANISM: Homo sapiens

-continued

```
<400> SEQUENCE: 3
atttattttc aatactcgct                                               20

<210> SEQ ID NO 4
<211> LENGTH: 27
<212> TYPE: DNA
<213> ORGANISM: Homo sapiens

<400> SEQUENCE: 4
tttgaccctc catgatcagg tccacct                                       27

<210> SEQ ID NO 5
<211> LENGTH: 23
<212> TYPE: DNA
<213> ORGANISM: Homo sapiens

<400> SEQUENCE: 5
cagaagactg tggatggccc ctc                                           23
```

DOUBLE-STRANDED SYNTHETIC OLIGONUCLEOTIDES USEFUL FOR INDUCING APOPTOSIS OF OSTEOCLASTS FOR THE TREATMENT OF OSTEOPENIC PATHOLOGIES

CROSS REFERENCE TO RELATED APPLICATIONS

This application is a National Stage of International Application No. PCT/IB2006/000741 filed on Mar. 30, 2006, claiming priority based on Italian Patent Application No. TO2005A000212, filed Mar. 31, 2005, the contents of all of which are incorporated herein by reference in their entirety.

The present invention relates to new therapeutically active substances capable of changing the molecular phenotype of osteoclasts, to pharmaceutical compositions containing the same and to their use in the treatment of osteopenic diseases resulting from primary hereditary defects or secondary conditions such as Paget's disease, osteolytic metastases of breast and prostate tumours, arthritis—such as for example arthritis caused by an increase in bone resorption and autoimmune arthritis-periodontitis, bone tumours and osteoporosis, such as for example postmenopausal osteoporosis and osteoporosis caused by hereditary diseases such as thalassaemia.

Osteoporosis is currently a social disease of major importance, particularly as far as the female population is concerned. The availability of a treatment which is potentially suitable for all the female population would therefore be highly desirable. In addition to this, in the case of individuals for whom there are no contra-indications but for whom there are risk conditions, such treatment should be appropriate for long-term treatment. It is furthermore expected that an effective therapeutic treatment against osteoporosis could also be of major interest to patients affected by thalassaemia major. It is in fact known that thalassaemia major is accompanied by changes in the skeleton's health, reflected in an increase in the risk of bone fractures (1-3). This has a multi-factor aetiology and culminates in a state of increased bone turnover, with excessive resorption and remodelling. Factors such as hormonal deficiency, expansion of the bone marrow, increased iron deposition, toxicity of desferrioxamine, calcium deficiency and vitamin D deficiency appear to play a key part in the skeletal disorders observed in thalassaemic patients. In addition to this, since the lifetime of these patients has been increased thanks to targeted treatments, osteoporosis is also becoming a serious problem for those individuals, both as regards prevention and early diagnosis, and as regards treatment.

Osteoporotic thalassaemia patients are currently treated with bisphosphonates, which exert a positive effect on osteoblasts, bone formation and mineralisation and at the same time inhibit bone osteoclast-mediated bone resorption. However, bisphosphonates have adverse effects, mainly affecting the digestive system, and have also been demonstrated to be ineffective in solving secondary problems associated with menopause.

The drugs currently used for the treatment of osteopenic diseases at least partly exert their mechanism of action through the activation of apoptosis of the cells which are responsible for bone resorption, i.e. osteoclasts (OCs).

In this respect, drugs designed to modulate the expression of the oestrogen receptor gene appear to be potentially of great interest, because, as is well known, oestrogen is involved in the regulation of the osteoclasts' phenotype. In particular it has been shown by experiment that oestrogen reduces the number of osteoclast precursors in the bone marrow, hinders the conversion of pre-osteoclasts into osteoclasts, encourages formation of the iso-form of the transforming growth factor TGF-$\beta_3$ (which is involved in the apoptosis of osteoclasts), suppresses the functional activity of osteoclasts and reduces expression of the genes activated by kB nuclear factor (NF-kB) which normally suppress apoptosis. In addition to this, it has been observed that the absence of expression of the oestrogen receptor $\alpha$ (ER$\alpha$) is associated with cortical osteopenia in adult mice and with a reduction in bone length.

However many drugs currently on the market for the treatment of osteopenic diseases have unresolved problems associated with side effects and route of administration. Among the main problems in conventional treatment for osteopenic diseases we mention:

determination of their long term safety,
reduced efficacy, for example in the case of nasal spray calcitonin,
gastrointestinal and oesophageal toxicity, especially in the case of some bisphosphonates, among which for example alendronate,
the possibility of limited use for early prevention,
excessive bone formation, for example in the case of fluorine salts,
the risk of venous thrombo-embolism and endometrial carcinoma, for example in the case of raloxifen,
the route of administration, which in general results in a low level of individual tolerance to particular types of administration (such as patches and sprays), for example in the case of calcitonin, bisphosphonates and oestrogens.

There is therefore a need to identify and therapeutically characterize compounds capable of effectively modifying the phenotype of the osteoclasts, which will therefore be effective in the treatment of osteopenic diseases without showing the abovementioned drawbacks.

The inventors have found that this need is satisfied by a synthetic double-stranded oligonucleotide characterised in that it comprises the nucleic acid sequence 5'-ATTTATTTTCAATACTGACT-3' (SEQ ID NO: 1) or a fragment or mutant thereof.

The abovementioned nucleic acid sequence corresponds to a stretch of the distal C promoter of the human oestrogen alpha receptor (ER$\alpha$) gene.

It has surprisingly been found that the synthetic double-stranded oligonucleotide of the invention is capable of increasing the expression of the ER-$\alpha$ gene, by the induction of osteoclasts apoptosis, but without giving rise to cytotoxic effects.

In a preferred embodiment, the synthetic double-stranded oligonucleotide comprises the abovementioned nucleic acid sequence (5'-ATTTATTTTCAATACTGACT-3' (SEQ ID NO: 1)) annealed to its complementary sequence (3'-TAAATAAAAGTTATGACTGA-5' (SEQ ID NO: 2)).

It has in fact been found that such a preferred oligonucleotide is capable of particularly effectively interacting with the nuclear factors involved in the regulation of the expression of the ER-$\alpha$ gene.

The synthetic double-stranded oligonucleotide of the invention may be synthesised using conventional chemical synthetic procedures. It may be synthesised as an oligonucleotide of DNA, i.e. in an unmodified form, or alternatively in a chemically modified form in order to increase its stability in biological fluids. In the latter case, nucleosides modified with protecting groups capable of protecting the chemical groups which are not desired to react can be used for the chemical synthesis of DNA, thereby obtaining modified DNA oligonucleotides, such as for example phosphorothioate or phosphoroamidate oligonucleotides.

Thus, the term "modified DNA oligonucleotide" is intended to mean a DNA oligonucleotide in which one or more of the nucleosides constituting the sequence are replaced by protecting groups. Procedures for the synthesis of modified oligonucleotides are known per se. Consequently, the synthesis of the modified DNA oligonucleotides falling within the scope of the invention does not require a detailed description, since it lies within the knowledge of the skilled in the art.

The synthetic double-stranded oligonucleotide of the invention can also be conveniently synthesised in the form of a chimeric PNA-DNA molecule, in which one of the complementary DNA strands is replaced by a peptide-nucleic acid strand (PNA). A peptide-nucleic acid is a DNA analogue having a pseudo-peptide skeleton instead of a sugar skeleton. A PNA mimics the behaviour of DNA and binds to complementary nucleic acid strands. Procedures for the synthesis of PNA and chimeric PNA-DNA molecules are known per se. Consequently, the synthesis of the chimeric PNA-DNA oligonucleotide according to the invention does not require a detailed description, since it lies within the knowledge of the skilled in the art.

As indicated previously, as an alternative to the preferred sequence 5'-ATTTATTTTCAATACTGACT-3' (SEQ ID NO: 1), the synthetic double-stranded oligonucleotide according to the invention may comprise a fragment or a mutant of this sequence. It has in fact been observed that oligonucleotides comprising a fragment or mutant of the above-mentioned preferred sequence may have the same ability to increase the expression of the ER-α gene, thereby inducing apoptosis of osteoclasts.

The fragments or mutants which are useful in the context of the invention are those fragments or mutants derived from the preferred sequence 5'-ATTTATTTTCAATACTGACT-3' (SEQ ID NO: 1) (for example by deletion or substitution of one or more nucleotides) which maintain the ability to bind to the same nuclear factors recognised by the sequence 5'-ATTTATTTTCAATACTGACT-3' (SEQ ID NO: 1), as shown by the EMSA (electrophoretic mobility shift-assay) and the South-Western blotting assays reported in the examples.

In particular, in the EMSA experiments it has been shown that the interaction between a double-stranded oligonucleotide comprising the sequence 5'-ATTTATTTTCAATACTGACT-3' (SEQ ID NO: 1) hybridised to its own complement (the preferred oligonucleotide) and nuclear factors, gives rise to a single major complex. The protein which binds to this preferred oligonucleotide is approximately 110 kd in South-Western assays.

In order to establish whether a fragment or mutant of the sequence 5'-ATTTATTTTCAATACTGACT-3' (SEQ ID NO: 1) has the ability to bind to the same nuclear factors which are recognised by the 5'-ATTTATTTTCAATACTGACT-3' sequence (SEQ ID NO: 1), the fragment or mutant, at issue in its double-stranded form, is added in stoichiometric excess (from 10 to 1000 folds) to an EMSA reaction (see examples) comprising the radioactively labelled preferred oligonucleotide and nuclear extracts. These competition experiments clarify the binding efficiency and specificity, since reduction of the delayed radioactive band leads to the conclusion that the tested fragment or mutant binds to the same nuclear factors with which the preferred oligonucleotide is able to interact.

Thus, fragments and mutants of the sequence 5'-ATTTATTTTCAATACTGACT-3' (SEQ ID NO: 1) which are useful in the context of this invention are those nucleic acid sequences derived from the sequence 5'-ATTTATTTTCAATACTGACT-3' (SEQ ID NO: 1) by deletion or substitution of one or more nucleotides, which in their double-stranded form are capable of effectively competing with the preferred oligonucleotide as defined above for binding to nuclear factors, as determined by competitive EMSA, and are capable of binding to a nuclear factor of approximately 110 kd, as determined by South-Western blotting.

For example, the mutant oligonucleotide 5'-ATTTATTTTCAATACTCGCT-3' (SEQ ID NO: 3) in its double-stranded form is capable of binding to the same nuclear factors as the preferred oligonucleotide indicated above and of stimulating the expression of the ER-α gene, which is important for the induction of apoptosis in osteoclasts.

Preferably, the fragment of the sequence 5'-ATTTATTTTCAATACTGACT-3' (SEQ ID NO: 1) which can be used in the context of the invention consists of at least 10 consecutive nucleotides of that sequence.

As previously mentioned, and as it will be described in greater detail in the section relating to the examples, the synthetic double-stranded oligonucleotides according to the invention (the expression "synthetic oligonucleotide" including DNA oligonucleotides, modified DNA oligonucleotides and chimeric PNA-DNA oligonucleotides) proved to be particularly effective in increasing the expression of the oestrogen alpha receptor gene and in inducing cell apoptosis in osteoclasts, without however showing cytoxic effects. Thus, these molecules may advantageously be used in therapeutic applications, in particular for the treatment of osteopenic diseases.

Thus, the use of a synthetic double-stranded oligonucleotide according to the invention for the preparation of a medicament for the treatment of osteopenic diseases, in particular Paget's disease, breast tumour osteolytic metastases, prostate tumour osteolytic metastases, arthritis, periodontitis, bone tumour and osteoporosis, falls within the scope of the present invention.

The use of a synthetic double-stranded oligonucleotide according to the invention for the preparation of a medicament suitable for increasing the expression of the oestrogen alpha receptor gene and/or capable of inducing cell apoptosis in osteoclasts also falls within the scope of the present invention.

In therapeutic applications which require the transfer of genetic material to the patient's cells, the synthetic oligonucleotides according to the invention may be used in the form of a complex with a vector capable of carrying the genetic material across the membrane of the target cells. Non-viral vectors, preferably lipid vectors, such as for example cationic liposomes, lipofectamines, liposheres or microspheres, are preferred for this purpose. Cationic liposomes are positively charged synthetic lipid vesicles which are capable of condensing nucleic acids in solution, thereby forming stable complexes, and which are capable of delivering the nucleic acid into the cell cytoplasm. Lipofectamines are a class of molecules known per se, which are formed of a polycationic tail to which the nucleic acid binds and a lipid portion which assists passage of the nucleic acid-lipofectamine complex through cell membranes.

Thus, a pharmaceutical composition comprising a synthetic double-stranded oligonucleotide according to the invention and a pharmaceutically acceptable carrier, the said synthetic oligonucleotide being optionally in the form of a complex with a lipid vector, preferably selected from cationic liposomes and lipofectamines, or with microspheres, also falls within the scope of the present invention.

The pharmaceutical composition of the invention includes a pharmaceutically acceptable carrier. This term is intended to include any pharmaceutically acceptable solvent or diluent, or any other additive which would be required, such as for example dispersing agents, coating agents, antibacterial agents, antifungal agents, preservatives, pH and/or tonicity adjusting agents, and the like.

The indicative concentration envisaged for the synthetic oligonucleotide in the composition according to the invention is comprised within the range of 10 to 300 nM.

The pharmaceutical composition according to the invention may be administered by various routes of administration depending upon whether systemic or local treatment is desired, and according to the areas requiring the treatment. Administration may be topical, oral or parenteral. Preferred routes of administration include the percutaneous route and local injection, optionally and restricted to some diseases together with orthopaedic surgery.

Furthermore, since a combined treatment with different modifiers of the transcription process allows to further increase the expression of the target genes, the pharmaceutical composition according to the invention may preferably comprise a further biomolecule which is capable of exerting a combined action on osteoclasts; this biomolecule is preferably selected from oestrogens, functional analogues of oestrogen, oestrene and oligonucleotides mimicking target sequences for the kB nuclear factor (NF-kB) as described in Penolazzi L. et al., Biochem Pharmacol. 2003 Oct. 1; 66:1189-98.

Among the functional analogues of oestrogen we would mention by way of example the selective oestrogen receptor molecules (SERMs), i.e. substances which are capable of specifically mimicking the effects of oestrogens on bone by binding to the oestrogen receptors of the bone but not those in other tissues, such as for example the reproductive tissues, and which are therefore devoid of any undesired effects. Among these there are for example tamoxifen and raloxifen, currently used as an anti-tumoural agent and an anti-osteoporotic agent, respectively. Other SERMs are currently in an advanced stage of clinical trials; these include tibolone, a synthetic analogue of ovary and testicle hormones which has the combined properties of oestrogen, progesterone and androgen.

As to the oligonucleotides which mimic target sequences for the kB nuclear factor, it has been shown that oligonucleotides capable of acting as decoy molecules against the NF-kB transcription factor induce apoptosis in human OCs. This effect is associated with the inhibition of IL-6 and the activation of caspase-3 (Penolazzi L. et al., Biochem Pharmacol. 2003 Oct. 1: 66:1189-98).

The following examples are provided by way of illustration and are not in any way intended to limit the scope of the claims as defined in the appended claims.

EXAMPLES

Cell Cultures

The experiments described were carried out on human osteosarcoma cell lines MG-63 and SaOS-2, mammary carcinoma cell lines MCF-7 and MDA-MB-231, primary human osteoblast cultures (OBS) and primary human osteoclast cultures (OCs). The cell lines and the primary cultures were maintained at 37° C. in an atmosphere with 80% humidity and in the presence of 5% $CO_2$.

Preparation of Primary OB Cultures

Primary osteoblast cultures were obtained from bone explants originating from surgical operations. These were reduced to small fragments and kept for approximately 2 weeks on Eagle's Minimum Essential Medium, supplemented with 20% FBS, streptomycin (50 µg/ml) and penicillin (100 µg/ml), fungizone (25 µg/ml) and vitamin C (10 µg/ml). When the cells achieved approximately 50-60% confluence, they were trypsinised, centrifuged at 1200 rpm for 10 minutes, re-suspended and placed in fresh flasks under the same culture conditions. Before and after the transfection experiments, the culture is tested for the presence of alkaline phosphatase, a marker of osteoblast differentiation (Lambertini, et al., Biochem Biophys Res Commun. (292: 761-770, 2002)).

Preparation of Primary OC Cultures

The primary osteoclast cultures were prepared as indicated by Matsuzaki et al., Endocrinology 1999; 140: 925-32, with some modifications. Mononuclear cells (PBMCs) were isolated from peripheral blood obtained from healthy consenting volunteers. Histopaque 1077 solution (Sigma) was used for the separation of the erythrocyte component. The recovered cells were resuspended in D-MEM/10% FCS, to a density of $3\times10^6$ cells/$cm^2$. After approximately 2 hours, the cells not adhered to the culture surface were removed. The monocytes so obtained were cultured in D-MEM/10% FCS supplemented with osteoclast differentiation inducers: 25 ng/ml M-CSF (macrophage colony-stimulating factor), 30 ng/ml RANKL (receptor activator of nuclear factor kappaB ligand), $10^{-7}$ M PTH (parathyroid hormone). After 14 days, the culture was tested for tartrase resistant acid phosphatase (TRAP) and for the expression of metalloproteinase 9 (MMP-9), two markers for the osteoclast phenotype. TRAP-positive cells having more than three nuclei were regarded as being mature osteoclasts (Penolazzi L, et al., Biochem Pharmacol. 2003 Oct. 1; 66: 1189-98).

Transfection of the Decoy Molecule

The cell lines and primary cultures were subjected to transient transfection using as the decoy molecule the double-stranded DNA oligonucleotide comprising the sequence 5'-ATTTATTTTCAATACTGACT-3' (SEQ ID NO: 1) annealed with its complement. This oligonucleotide will subsequently be referred to as the "decoy oligonucleotide". The cationic liposome PC:DOTAP was used as a carrier (Piva R, et al., J. of Steroid Biochem. and Mol. Biol. (75: 121-128, 2000)). The cells were transfected with the decoy oligonucleotide (usually 600 ng/ml with 2.5 µg of PC:DOTAP). When transfection was complete, the cells were washed with PBS 1× (136 mM NaCl, 2.68 mM KCl, 1.76 mM $KH_2PO_4$, 10.14 mM $Na_2HPO_4$) and were analysed after 24 hours.

Quantitative RT-PCR

This technique was used to check the ER-α expression levels. To carry out this analysis, the cells were reduced to pellets, lysed and subjected to extraction of the corresponding total RNA with the SV Total RNA Isolation System. The total RNA was reverted to cDNA for use in quantitative Real Time-PCR, with the "Superscript Preamplification System" kit (INVITROGEN™). Real time RT-PCR, which is not only capable of amplifying specific sequences but also of quantifying cDNA in real time, was carried out using the TaqMan technology which involves the use of oligonucleotide probes (ER-α: 5'-TTT GAC CCT CCA TGA TCA GGT CCA CCT-3' (SEQ ID NO: 4), GAPDH: 5'-CAG AAG ACT GTG GAT GGC CCC TC-3' (SEQ ID NO: 5)) which are complementary to the target genes and which are labelled at the 5' end with a fluorescent reporter dye (FAM, 6-carboxyfluorescein for ER-α, VIC for GAPDH) and at the 3' end with the quencher dye (TAMRA, 6-carboxy-tetramethylrodamine) which quenches the fluorescence of the former dye until the 5'-endonuclease activity of the Taq DNA polymerase separates them.

Immunocytochemical Analysis

Immunocytochemical analysis was carried out with the Polyvalent-HRP Ultrastain immunostaining kit system using the streptavidine-biotin method. The cells were cultured on 1.7 $cm^2$ slides; 48 hours after transfection, they were fixed with cold 100% methanol and permeabilised with 0.2% (v/v) Triton X-100 in TBS (Tris-buffered saline: 2.6 mM KCl, 0.1 M NaCl, 25 mM Tris HCl). This was followed by incubation to inhibit endogenous pyroxidases in 3% $H_2O_2$, and transferred to the blocking solution provided by the kit. The suitably diluted specific antibody was added for 48 hours at 4° C. in a moist chamber. The cell layer was then incubated with "Anti-polyvalent Biotinylated Antibody" at room temperature; there then followed another incubation in Streptavidine HRP and finally addition of the substrate-chromogen mixture (AEC Chromogen kit). The reaction was allowed to proceed for a period of time which varied between 5 and 10 minutes until the desired intensity of colour was achieved and then it was blocked by washing in TBS. The slides were preserved in 9:1 glycerol/PBS.

Cytotoxicity Assay

Cytotoxic activity was evaluated on culture cells using the MTT assay after 3 days of treatment with 0.2, 0.4, 1 and 2 µg/ml of the decoy oligonucleotide complexed with PC:DOTAP. The cells were incubated at 37° C. for approximately 2 hours with 25 µl of MTT (3-(4,5-Dimethylthiazol-2-yl)-2,5-diphenyltetrazolium bromide; thiazol blue) (5 mg/ml in PBS 1×); subsequently they were incubated for a further 12 hours, again at 37° C. with 100 µl of lysis buffer (20% SDS in 50% DMF pH 4) and then spectrophometrically read at 570 nm.

Apoptosis

The "DeadEnd™ Colorimetric TUNEL System" which measures the degree of fragmentation of the DNA was used for the analysis of apoptosis.

The cells, cultured and treated on 0.8 $cm^2$ slides, were fixed by incubation at room temperature for 25 minutes in a solution containing 4% paraformaldehyde. Then, after washing with PBS, the cells were permeabilised with a 0.2% solution of Triton X-100 in PBS. This was followed by equilibration for 5-10 minutes in 100 µl of Equilibration Buffer (200 mM potassium cacodilate pH 6.6; 25 mM Tris HCl pH 6.6; 0.2 mM DTT, 0.25 mg/ml BSA, 2.5 mM cobalt chloride). The layer of cells was then layered with "TdT Reaction Mix" containing the enzyme Terminal-deoxynucleotidyl-transferase (TdT) and the components required for the reaction (98 µl of Equilibration Buffer, 1 µl Biotinylated Nucleotide Mix, 1 µl of TdT enzyme), protected by a plastic cover slip and incubated at 37° C. for 60 minutes in a moist chamber. The reaction was blocked by immersing the slide in SSC 2× (20× SSC: 87.7 g NaCl, 44.1 g sodium citrate) for 15 minutes at room temperature. Then, the slide was immersed in 0.3% hydrogen peroxide for 3-5 minutes at room temperature to block the endogenous pyroxidases which could falsify the experimental results. The cells were then layered with 100 µl of "Streptavidine-HRP" (1 µg/ml) and left at room temperature for 30 minutes. Finally, the slide was placed in contact with the diaminobenzidine chromogenic solution (DAB) (50 µl of DAB substrate 20× Buffer, diluted in 950 µl of deionised water, 50 µl of DAB chromogen 20×, 50 µl of $H_2O_2$ 20×) until the desired intensity of colour was achieved. The reaction was blocked in PBS 1× and the slide was then mounted in 100% glycerol. In the case of Ocs, apoptosis was calculated as the apoptotic nuclei to total nuclei ratio for TRAP-positive cells having more than three nuclei.

The level of apoptosis was also measured by immunocytochemical evaluation of the levels of Caspase 3 (Boatright K M, Salvesen G S. Curr Opin Cell Biol. (15: 725-731, 2003)).

EMSA (Electrophoretic Mobility Shift-Assay)

The decoy oligonucleotide was labelled with $\gamma^{32}P$ ATP (NEN) at the 5' end. Approximately 0.1 ng of decoy oligo (6000 cpm) were incubated with nuclear extracts of MDA-MB231 mammary carcinoma cells in the presence of 10 mM Tris-HCl pH 7.5, 20 mM KCl, 10 mM $MgCl_2$, 10 mM DTT, 5 mM EDTA, 0.01% Triton X100, 0.5% glycerol, supplementary with 1.2 µg of poly(dI-dC)-poly(dI-dC): the reaction was carried out at room temperature for 1 hour. The unlabelled competitor (unlabelled decoy oligo) was added up to a 1000-fold molar excess. The DNA-protein complex was separated from the unbound DNA by 6% polyacrylamide gel electrophoresis in 0.25× Tris-borate-EDTA (TBE) buffer. The gel was then dried and autoradiographed. In the EMSA experiments carried out, it was found that the interaction between the radioactively labelled double-stranded oligonucleotide comprising the sequence 5'-ATTTATTTTCAATACTGACT-3' (SEQ ID NO: 1) and the nuclear factors gives rise to a single major complex which was efficiently displaced by a stoichiometric excess of the same non-radioactive oligonucleotide, but not by non-correlated oligonucleotides consisting of sequences recognised by other transcription factors, for example Sp1.

South-Western Blotting

Nuclear extracts of MDA-MB231 mammary carcinoma cells were analysed by SDS-PAGE. After electrophoretic migration the proteins were transferred onto nitrocellulose and subjected to a denaturing solution (6M Guanidine HCl, 25 mM Hepes pH 7.9, 3 mM $MgCl_2$, 4 mM KCl and 1 mM DTT), to achieve renaturation. To identify the proteins capable of binding to the decoy oligo, the nitrocellulose filter was incubated with a blocking solution (25 mM Hepes pH 7.9, 3 mM $MgCl_2$, 4 mM KCl, 1 mM DTT and 5% of powdered milk) for 30 min at 4° C.; then this filter was incubated overnight at 4° C. in a binding buffer containing 25 mM Hepes pH 7.9, 3 mM $MgCl_2$, 4 mM KCl, 1 mM DTT, 0.25% of powdered milk and the radioactively labelled decoy oligonucleotide (approximately $10^6$ cpm/ml). The next day the filter was subjected to 3 washes in binding buffer for 10 min and subsequently autoradiographed. The protein binding this oligonucleotide proved to be of approximately 110 kd in the south-western blotting experiments.

Results

The results obtained are illustrated in the following tables. The biological activity of the decoy oligonucleotide was evaluated by examining the ability of this molecule to induce the expression of ERα in ERα-negative (MDA-MB-231), ERα-positive (MCF-7) mammary carcinoma and osteosarcoma (MG-63 and SaOS-2) cell lines. This analysis was carried out by Real Time RT-PCR. The cells were transfected with 900 ng/ml of decoy oligonucleotide for 48 hours. Total transcription levels for hERα were evaluated with Real Time RT-PCR. The results of the experiment are shown in Table 1. In the table the data are expressed in terms of amplificate-induction folds with respect to the control. It can be observed that a significant increase in the levels of expression was found in all the cell lines following treatment with decoy oligo.

TABLE 1

Induction of total transcription levels by hERα

| Cell line | Control | + decoy oligo |
|---|---|---|
| MDA-MB-231 | 1 | 81.1 |
| MCF-7 | 1 | 2.4 |
| MG-63 | 1 | 1.5 |
| SaOS-2 | 37 | 278 |

The decoy oligonucleotide was then tested for any cytotoxic effects. For this purpose, the effect of the decoy oligonucleotide on the vitality of human osteoclast cell cultures (Penolazzi L, et al., Biochem Pharmacol. 2003 Oct. 1; 66: 1189-98) treated with 0.2, 0.4, 1 and 2 μg/ml of decoy oligonucleotide complexed with PC:DOTAP was evaluated. After 72 hours, the percentage of surviving cells was evaluated by MTT testing. Table 2 shows the results obtained, expressed in terms of the % of non-surviving cells. As it may be observed from the data shown in Table 2, no significant cytotoxic effects were observed.

TABLE 2

Toxicity of the decoy oligo
(% of non-surviving cells)

| 200 ng/ml | <3% |
| 400 ng/ml | <3% |
| 1 μg/ml | <3% |
| 2 μg/ml | <3% |

Then, the ability of the decoy oligonucleotide to induce apoptosis in human osteoclasts was evaluated. Primary cultures of human osteoblasts and osteoclasts were transfected with 900 ng/ml of decoy oligonucleotide complexed with PC:DOTAP, for 48 hours. After 24 hours of treatment, the levels of apoptosis in the cell populations were evaluated by TUNEL testing (Penolazzi L, et al., Biochem Pharmacol. 2003 Oct. 1; 66: 1189-98) (Table 3) and by analysis of the levels of the enzyme Caspase 3 (Table 4), whose increase is known to be associated with the apoptotic process (Boatright K M, Salvesen G S. Curr Opin Cell Biol. (15: 725-731, 2003)). As it may be observed from the data shown in Table 3, the decoy oligonucleotide is capable of inducing cell apoptosis in human osteoclasts.

TABLE 3

| | % of apoptotic osteoclasts | | % of apoptotic osteoblasts |
|---|---|---|---|
| Control | 6.6 ± 1.75 | Control | 0.5 ± 0.02 |
| + decoy oligo | 70.3 ± 2.14 | + decoy oligo | 0.5 ± 0.01 |

Finally, the ability of the decoy oligonucleotide to induce both the expression of Caspase 3 and the expression of both isoforms of the oestrogen receptor was evaluated by immunocytochemical analysis. Primary cultures of osteoclasts transfected with 900 ng/ml of decoy oligo complexed with PC:DOTAP for 48 hours were immunocytochemically analysed using anti-Caspase 3, anti-hERα and anti-hERβ monoclonal antibodies. Table 4 shows the levels of expression (+=low; +++=high; ++++=very high) obtained upon treatment, evaluated with the Ultraystain Kit (Ylem) detection system.

TABLE 4

Immunocytochemical analysis

| | Caspase 3 | HERα | hERβ |
|---|---|---|---|
| Control | − | + | + |
| + decoy oligo | +++ | ++++ | +++ |

The invention claimed is:

1. A synthetic double-stranded oligonucleotide comprising the nucleotide sequence of SEQ ID NO: 3.

2. The synthetic double-stranded oligonucleotide according to claim 1, wherein said synthetic double-stranded oligonucleotide is a DNA oligonucleotide, a modified DNA oligonucleotide or a chimeric PNA-DNA oligonucleotide.

3. The synthetic double-stranded oligonucleotide according to claim 2, wherein said modified DNA oligonucleotide is a phosphorothioate or phosphoroamidate DNA oligonucleotide.

4. A pharmaceutical composition comprising the synthetic double-stranded oligonucleotide according to claim 3 and a pharmaceutically acceptable carrier.

5. The pharmaceutical composition according to claim 4, wherein said synthetic double-stranded oligonucleotide is in the form of a complex with a lipid vector or with micro spheres.

6. The pharmaceutical composition according to claim 4, wherein said synthetic double-stranded oligonucleotide is present at a concentration of 10 to 300 nM.

7. The pharmaceutical composition according to claim 4, further comprising a biomolecule selected from the group consisting of oestrogens, functional analogues of oestrogens, oestrene and oligonucleotides mimicking target sequences for the kB nuclear factor (NF-kB).

* * * * *